(12) United States Patent
Riddle

(10) Patent No.: US 7,765,871 B2
(45) Date of Patent: Aug. 3, 2010

(54) SYSTEM AND METHOD FOR GAS ANALYSIS USING PHOTOACOUSTIC SPECTROSCOPY

(75) Inventor: Alfred Riddle, Milpitas, CA (US)

(73) Assignee: Finesse Solutions, LLC, San Jose, CA (US)

( * ) Notice: Subject to any disclaimer, the term of this patent is extended or adjusted under 35 U.S.C. 154(b) by 467 days.

(21) Appl. No.: 12/006,681

(22) Filed: Jan. 4, 2008

(65) Prior Publication Data

US 2008/0134756 A1   Jun. 12, 2008

(51) Int. Cl.
*G01N 29/02* (2006.01)
*G01N 29/04* (2006.01)

(52) U.S. Cl. ............... 73/590; 73/24.02; 73/24.06; 73/579

(58) Field of Classification Search ......... 73/24.01, 73/24.02, 24.06, 579, 589, 590
See application file for complete search history.

(56) References Cited

U.S. PATENT DOCUMENTS

| 3,445,595 | A * | 5/1969 | Barnes et al. ............ 381/113 |
| 4,399,689 | A * | 8/1983 | Bechthold et al. ......... 73/24.02 |
| 6,877,375 | B2 * | 4/2005 | Greenwood ............... 73/597 |
| 6,937,340 | B2 * | 8/2005 | Roudil et al. ............ 356/432 |
| 7,263,871 | B2 * | 9/2007 | Selker et al. ............ 73/24.02 |
| 7,398,672 | B2 * | 7/2008 | Riddle ................... 73/24.06 |
| 7,520,158 | B2 * | 4/2009 | DiFoggio ................ 73/19.1 |
| 2006/0123884 | A1 | 6/2006 | Selker et al. |
| 2010/0027012 | A1 * | 2/2010 | Fritz et al. ............. 356/432 |

OTHER PUBLICATIONS

Bijnen et. al. "Geometrical Optimization of a longitudinal resonant Photoacoustic Cell for sensitive and fast Trace Gas detection" Review of Scientific Instruments AIP, Melville, NY US vol. 67, No. 8 i Aug. 1996 pp. 2914-2923.
Miklos, et. al. "Application of Acoustic Resonators in Photoacoustic resonators in Photoacoustic Trace gas Analysis and Metrology" Review of Scientific Instruments AIP Melville, NY USA vol. 72, No. 4 Apr. 2001 pp. 1937-1955 cited in application.
Firebaugh et al, "Miniaturization and Integration of Photoacoustic detection with a Microfabricated Chemical Reactor System" Journal of Microchemical Systems, IEEE vol. 10, No. 2 Jun. 2001 pp. 232-236.
Zeninara et. al. "Design and Characteristics of a Differential Helmholtz Resonant Photoacoustic Cell for Infrared Gas Detection" Infrared Physics and Technology, Elsevier Science, G.B. vol. 40 No. 1 Feb. 1999 pp. 1-23.

* cited by examiner

*Primary Examiner*—J M Saint Surin
(74) *Attorney, Agent, or Firm*—Herbert Burkard

(57) ABSTRACT

A system and method for analyzing a target analyte gas concentration using a photoacoustic spectroscopy cell comprising:
i) a modulatable light source which provides optical radiation at an absorption wavelength of a target analyte;
ii) a resonant acoustic chamber for containing said analyte;
iii) a microphone positioned within said chamber whereby the acoustic reactance of the microphone is a substantial factor in determining the acoustic resonant frequency of the acoustic chamber and where the magnitude of the acoustic reactance of the microphone is at least two times the acoustic resistance of the microphone.

21 Claims, 9 Drawing Sheets

SYSTEM AND METHOD FOR GAS ANALYSIS USING PHOTOACOUSTIC SPECTROSCOPY

RELATED APPLICATIONS

This application claims priority from co-pending, commonly assigned application Ser. No. 11/485,129 filed 12 Jul. 2006.

FIELD OF THE INVENTION

The present invention relates generally to the field of analyte detection and concentration analysis and to an improved apparatus for performing same. In one preferred embodiment, the present invention relates especially to gas contaminant detection, e.g., trace moisture in a semiconductor process gas.

BACKGROUND OF THE INVENTION

As semiconductor technology advances and device sizes shrink, the impact of contaminants in the gases used to fabricate these devices becomes increasingly important. Many specialty gases are used in the production of semiconductor devices. For example, a major source of contamination in the chip fabrication process is the presence in process gases of trace amounts, e.g., on the order of tens of parts per billion by volume (ppbv), of water. While ultra pure (water and other contaminant free) gases are sometimes available, chemical reactions, phase changes, and other effects often result in the presence of moisture in a gas supply line of a semiconductor fabrication system. These facts make it very attractive to have moisture sensors that are small, efficient, have rapid response times, and are inexpensive enough to be placed in multiple locations in the system. These locations include each line of the gas box and also immediately before the reactor of a semiconductor fabrication system. Currently available sensors do not meet all the aforementioned requirements.

The ambient atmosphere typically contains water vapor concentrations of up to, or even exceeding, approximately 1%. This is at least six orders of magnitude greater than the acceptable limits for most semiconductor process gases. As such, even very small leaks of ambient air into the gas distribution system may introduce significant moisture contamination. Furthermore, even well-dried gas lines can contribute moisture to an otherwise high-purity gas. After a gas distribution system is purged with an inert gas, some water molecules can remain in the lines due to strong binding to adsorption sites on metal and metal oxide surfaces. Subsequently, when polar gases such as HBr and HCl enter the feed gas lines, they tend to displace water molecules, which then enter the feed gas stream. Additionally, surface oxides within the gas distribution system can interact with corrosive gases to create water molecules by chemical reactions such as the following:

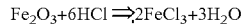

$$Fe_2O_3 + 6HCl \Rightarrow 2FeCl_3 + 3H_2O$$

Since even dry components within the distribution system can spontaneously create water, it seems clear that the semiconductor industry needs real time, in-line moisture monitors to protect wafer fabrication systems from moisture contamination.

Semiconductor fabs require as many as 50 gases to process a wafer. Table 1 lists some of the gases associated with different process steps. Contaminants in these gases can diminish yields and degrade chip reliability. Purity requirements for process gases will likely become even more strict as chip line widths continue to shrink. As indicated, one common contaminant is water vapor which can distort manufacturing processes and thereby compromise device performance. Process steps which are vulnerable to moisture contamination include epitaxial growth, sputtering, metal-organic vapor phase epitaxy, thermal etching, gas phase etching of tungsten films, plasma etching of silicon and polysilicon, and chemical vapor deposition of polysilicon, silicon dioxide, silicon nitride, and tungsten. The presence of water can accelerate or retard the chemical reactions which occur during deposition or etching, thereby altering the thickness and/or composition of critical layers. Moisture can create pitting, hazing, and stacking faults; cause resist patterns to fail; induce diodes and junctions to leak; and otherwise degrade the service lifetime of products which pass inspection and reach the marketplace.

TABLE 1

Process Steps and Associated Gases

| Process Steps | Gases (Inert Gases, Hydrides, and Corrosives) | |
|---|---|---|
| Oxidation | Carriers | Ar, N, |
| | Reactants | $Cl_2$, $H_2$, HCl, $O_2$ |
| Photolithography | Carriers | Ar, $N_2$, |
| Etching | Plasma or | Ar, $BCl_3$, $Cl_2$, $CF_2$, $CF_4$, $C_2F_6$, |
| | Reactive Ion Etching | He, $H_2$, $N_2$, $O_2$, $C_2F_8$, $SiF_4$, $SF_6$ |
| | Carriers | Ar, $H_2$, Ne, Xe |
| Diffusion | Carriers | Ar, $H_2$, $N_2$, $O_2$ |
| | Dopant Sources | $AsH_3$, $BCl_3$, $B_2H_6$, $PH_3$ |
| Chemical Vapor | Oxidation | $CO_2$, $N_2$, $O_2$, $H_2SiCl_2$, $SiH_4$ |
| Deposition | Doping | $AsH_3$, $B_2H_6$, , $PH_3$, $SiH_4$ |
| | Nitride | $N_2O$, $SiCl_4$, $NH_3$ |
| | III-V Layers | $AsH_3$, $H_2$, HCl, $H_2S$, $PH_3$ |
| Ion Implantation | | Ar, $AsH_3$, $BCl_3$, $BF_3$, $B_{11}F_3$, $Cl_2$, He, $H_2$, $H_2S$, $N_2$, $PH_3$, $SiH_4$, $P_2F_6$, $SiF_4$ |
| Annealing | | Ar, $H_2$, $N_2$ |
| Metallization | | Ar |
| Bonding | | Ar, $H_2$, $N_2$ |
| Crystal Growth | | Ar, He, $H_2$ |
| Epitaxy | Carriers | Ar, $H_2$, $N_2$ |
| | Silicon Sources | $SiH_4$, $H_2SiCl_2$, $HSiCl_3$, $SiCl_4$ |
| | Dopants | $AsH_3$, $B_2H_6$, $PH_3$ |
| | Etchant | HCl |

Additionally, moisture will react with certain process gases, yielding acids which corrode gas handling equipment. For example, aqueous hydrochloric acid attacks iron and other constituents of stainless steel. As corrosion advances, pipes, valves, mass flow meters, mass flow controllers, and other components can fail, causing equipment downtime. Furthermore, corroded pipes release particles which enter the gas stream. Gas-phase nucleation by particles and flaking of particles from gas lines onto wafers can reduce yield. According to one report, the gas distribution system accounts for 68% of all contamination in CMOS processes. Moisture in arsine and phosphine lines may also contaminate the ultrahigh-vacuum chambers used for doping wafers. Water molecules in the chamber can make it impossible to draw a sufficiently high vacuum, forcing engineers to shut down the chamber and subject it to an extended bake.

Manufacturers of LED's and VCSELs generally deposit three to five epitaxial layers by organometallic vapor phase epitaxy, using ultra-high-purity anhydrous ammonia as a process gas. Trace oxygen in the epitaxial layers can limit device performance. The photoluminescence of LED's and VCSELs depend strongly on the moisture content of the ammonia used during production and therefore to increase the efficiency, the amount of moisture needs to be accurately monitored during production.

Kermarrec and co-workers have studied the effect of moisture on SiGe devices. In their words, "A direct correlation between moisture impurity in process gases and atomic oxygen present in epitaxial SiGe layers was demonstrated, both qualitatively and quantitatively. The resulting incorporation of oxygen atoms can induce dislocations into the strained layers, which may degrade device performance and, subsequently, reliability." O. Kermarrec et. al., *Solid State Technology*, 45(3). Pp. 55-60, 2002.

Sensors for process gases in the semiconductor industry should advantageously have the following characteristics:
- be sensitive enough to detect moisture or other contaminants in concentrations of <10 parts per billion by volume (ppbv),
- be fast enough to react to changes in gas flows that may last less than 30 seconds,
- be small enough (<1 ft$^3$, or 0.029 m$^3$) to fit among the gas lines and the surrounding areas,
- be quick-drying enough to return the process tool that it monitors to productive use within an hour, and inexpensive enough (<$10,000) to be placed at multiple locations.

Unlike the sensor design of the present invention, the prior art designs have been unable to fulfill all these requirements Moisture sensors (monitors) are often referred to as "in-line" or "at-line". Generally, in-line refers to a monitor that is in the gas line such that the gas under test passes through the monitor without a need for tapping off the line. The term at-line is generally used for monitors that tap some flow off of the gas line. The flow that is tapped off is generally discarded. Both in-line and at-line monitors for semiconductor industry process gases should advantageously have the above-indicated characteristics, which are not available with current technologies. Since none of the technologies available today can satisfy all of these criteria and therefore do not meet the needs of fab operators, it is not surprising that wafer fabs rarely deploy in-line monitors. The present invention satisfies an unmet industry need by providing a system which meets all four requirements (sensitivity, speed, size, and price) and is suitable for both in-line and at-line sensors.

Of course, the detection of trace contaminants or other target analytes present in a liquid or solid matrix is also a matter of significance in a wide variety of industrial, medical, academic and defense contexts. Although the present invention will be discussed primarily in the context of analyte detection in a gaseous medium, it is to be understood that the unique photoacoustic apparatus and method of the present invention is suitable for the detection of target analytes present in a gaseous, liquid or solid matrix. Furthermore, although the present invention will be described primarily in the context of moisture detection, it should be recognized that it is applicable to the detection of essentially any fluid (i.e., gas or liquid) that is photoacoustically active and whose absorption peak or peaks coincide with the emission frequency of an available light source capable of supplying optical energy.

Photoacoustic Spectroscopy (PAS) studies optical events which through non-radiative transitions have become acoustic events. The molecules of any given compound absorb light at specific wavelengths characteristic of the compound and undergo quantized vibrational or rotational transitions. They gain kinetic energy in the form of heat, and collide with other neighboring molecules thereby creating a pressure wave. Since a pressure wave in a gaseous or liquid medium is sound, it can be detected by a microphone. As used in the present invention, the term "microphone" connotes any acoustic sensing mechanism capable of detecting a pressure wave or velocity in a gaseous or liquid medium. Examples include electric and diaphragm microphones and piezoelectric transducers. The sensitivity of a PAS instrument is determined primarily by: i) the efficiency with which the optical excitation produces a pressure wave in the fluid (i.e., gas or liquid) contained in an acoustic chamber, and ii) the efficiency with which the acoustic wave is converted into an electrical signal. In the simplest case these efficiencies can be multiplied to determine the total instrument efficiency. In the most general case the microphone contains moving parts which affect the total acoustic impedance of the PAS instrument so the total instrument efficiency can only be determined by including the interaction between the microphone and the acoustic chamber.

In order to further elucidate the photoacoustic effect it is useful to consider the physical steps that result in a photoacoustic signal. The photoacoustic effect in a photoacoustic chamber (often although not invariably in the form of a tube) can be divided into four sequential events: 1) absorption of incident optical radiation by a target analyte molecule; 2) heat release due to transformation of the absorbed light energy into molecular motion; 3) pressure wave generation due to heat induced expansion of the fluid present in the acoustic chamber; and 4) detection of the acoustic signal generated by the pressure wave. In the context of the present invention, it should be understood that the target analyte can be a gas or liquid which is: i) dispersed in a gas or liquid which fills the acoustic chamber, or ii) dispersed in a solid matrix which is contained within a gas filled acoustic chamber.

Alexander Graham Bell discovered the photoacoustic (Tyndall-Roentgen) effect in 1881. However, scientific and technological interest in the effect lay dormant for approximately 80 years in the absence of suitable light sources and microphones. In the 1960's, lasers stimulated researchers to explore using the photoacoustic effect for spectroscopic analysis. In 1968, Kerr and Atwood were able to detect low concentrations of pollutants in air by using lasers and phase-sensitive, lock-in acoustic detection techniques. (E. L. Kerr, and J. G. Atwood, "The laser illuminated absorptivity spectrophone: a method for measurement of weak absorptivity in gases at laser wavelengths," *Applied Optics*, No 7, p. 915-921, 1968. Kreuzer detected methane in nitrogen in 1971, using an intensity-modulated He—Ne laser (L. B. Kreuzer, "Ultralow gas concentration infrared absorption spectroscopy," *J. Applied Physics*, Vol. 42, p. 2934-2943, 1971. See also: Aniko Veres, Zoltan Bozoki, Arpad Mohacsi, Miklos Szakall and Gabor Szabo; External Cavity Diode Laser Based Photoacoustic Detection of CO2 at 1.43 um: The Effect of Molecular Relaxation; Applied Spectroscopy, Vol. 57, No. 8, pp. 900-905, 2003. Per Ohlckers, Alain. M. Ferber, Vitaly K. Dmitriev and Grigory Kirpilenko; A Photoacoustic Gas Sensing Silicon Microsystem; Transducers 2001, Jun. 10-14, 2001. P. D. Goldan and Kito Goto; An acoustically resonant system for the detection of low-level infra-red absorption in atmospheric pollutants; J. Appl. Physics; Vol. 45; No. 10; pp. 4350-4355, October, 1974. J.-P. Besson, S. Schilt, L. Thevenaz; Multi-gas Sensing Based on Photoacoustic Spectroscopy using Tunable Laser Diodes; Spectrochemica; Vol. 60; pp. 3449-3456; 2004. Lars-Goran Rosengren; Optimal Optoacoustic Detector Design; Applied Optics; Vol. 14; No. 8; pp. 1960-1976; August, 1975. M. Szakall, Z. Bozoki, M. Kraemer, N. Spelten, O. Moehler, and U. Schurath; Evaluation of a Photoacoustic Detector for Water Vapor Measurements under Simulated Tropospheric Conditions; Environ. Sci. Tech.; Vol. 35; No. 24; pp. 4881-4885; 2001. A. Miklos, P. Hess, Z. Bozoki; Application of Acoustic Resonators in Photoacoustic Trace Gas Analysis and Metrology; Rev. Sci. Instru., Vol. 72; No. 4; pp. 1937-1955; April 2001. M. Sigrist; Laser Generation of Acoustic Signals in Liquids and Gases; J. Appl. Phys.; Vol. 60; No. 7; pp. R83-R121; October 1986. M. Sigrist; Trace Gas Monitoring by Photoacoustic and Related Techniques; Rev. Sci. Instr.; Vol. 74; No. 1; pp. 486-490; January 2003. M. Nagale and M. Sigrist, Mobile Laser Spectrometer with Novel Resonant Multipass Photoacoustic Cell for Trace-Gas Sensing; Appl. Phys. B; Vol. 70; pp. 895-901; June 2005. S. L. Firebaugh; Miniaturization and Integration of Photoacoustic Detection; Ph.D. Thesis; MIT, May 2001.

As is apparent from the numerous above-cited references, there is a large body of work on both the theoretical fundamentals of photoacoustic spectroscopy, and also on the physical systems that have heretofore been used to carry out photoacoustic spectroscopy. Several companies sell PAS based detection systems, comprising either an incoherent or coherent light source, an acoustic cell, a microphone and means (usually a transducer) to convert a pressure to a voltage, and electronics to collect data and to digitize the output signal from the transducer. Researchers have utilized these systems to explore applications in environmental monitoring, life sciences, and medicine. Historically, the most sensitive systems employ large, high-power (>2 W) CO or $CO_2$ lasers. Widely deployable systems, however, will require compact and inexpensive light sources.

In 1996, a group at the Hungarian Academy of Sciences reported using a photoacoustic cell situated inside the optical cavity of a diode laser to achieve a significant gain in detection efficiency compared to extracavity operation. (Z. Bozoki, et. al., *Appl. Phys., B* 63, 399 (1966). The same group later described a PAS system which supplied optical power with a DFB laser (M. Szakall, Z. Bozôki, A. Mohâcsi, A. Varga, and G. Szabô, "Diode Laser Based Photoacoustic Water Vapor Detection System for Atmospheric Research," *Applied Spectroscopy*, Volume 58, Number 7, 792-798, 2004). This system reportedly was able to detect moisture at levels of about 250 ppbv and would therefore appear to have come within a factor of about 25 of the minimum required sensitivity for semiconductor gases, but did not meet the criteria for industrial use in terms of size or cost.

It is known that the configuration of the cell in which the gas is contained can influence the detection process. The first cells used to detect gaseous analytes were simple cylinders with windows at each end which were more or less transparent to the optical excitation beam. The optical signal entering the cell was modulated to induce a pressure wave at an acoustic resonance frequency of the cell and this pressure wave detected using a microphone affixed to the interior wall of the cell. Prior art workers sought to optimize this design by analyzing the pressure variation within the cell structure caused by the optical excitation beam and adjusting the microphone placement to be at the site of maximum pressure hoping to thereby maximize the microphone output voltage or current for a given optical modulation frequency. The designs of the prior art utilized the microphone as a mere "observer" which simply registered the pressure changes within the cell without affecting the result. Indeed, the prior art sought in most cases to have the microphone's effect on the cell acoustic resonance frequency be as small as possible. The prior art also sought achieve maximum power transfer to the microphone, which I have found is undesirable since this inherently draws the maximum energy out of the cavity. Moreover, the prior art did not realize that the detection sensitivity can be maximized by causing the microphone to form a integral part of the resonant system as opposed to considering only the cell itself without a microphone. A recent article (FGC Bijnen et. al.: "Geometrical Optimization of a Longitudinal Resonant Photoacoustic Cell for Sensitive and Fast Trace Gas Detection" Review of Scientific Instruments Vol. 67, No. 8 1 Aug. 1996, pp 2914-2923) used an electrical circuit equivalent of the cell and microphone to determine the negative effect of the microphone on the performance (peak pressure) of a previously optimized acoustic chamber. In contradistinction, I have specifically found that the photoacoustic cell response can be enhanced by causing the microphone to be an integral part of the resonant acoustic cell as opposed to being merely a passive monitor of the pressure wave developed in the acoustic cell. This provides a number of advantages including a significant reduction in the size of the instrument and/or an enhancement of its sensitivity. As used herein the term "instrument" connotes the acoustical cavity plus the light source, modulation means, microphone while the terms "cavity" and "chamber" connote the acoustic volume in resonance, and "cell" the acoustic volume in resonance with walls, windows, and microphone and possible connecting tubes. The term "microphone" includes, but is not limited to, diaphragm and electrets.

Light sources may be modulated directly or externally. The particular light source modulation method is not a determining factor in the practice of this invention and many different modulation schemes are known to those skilled in the art. Direct modulation means that the optical source power output or wavelength is changed by directly changing the operating current or temperature of the source. External modulation means that a device outside of the light source is used to change the power or phase of the light source. External amplitude modulation is suitably achieved by a shutter and external phase modulation is often achieved by passing the light source through one of various electro-optic materials. The type of light source modulation is not essential to this invention, and either type of modulation is suitable. The various methods of both direct and external modulation are described in the literature and are known to those skilled in the art.

The light source modulation frequency is set by the cell acoustic resonance frequency. The light source modulation frequency must equal a resonant frequency of the acoustic cell. However, the particular light source modulation frequency is not a determining factor in this invention. The light source modulation frequency is also affected by the detection scheme chosen (typically either 1f or 2f). The selection of a particular detection scheme will be influenced by available lasers, target analytes, available power sources, and/or system size constraints. If external amplitude modulation is chosen the source modulation frequency will typically be chosen to be equal to the cell acoustic resonance frequency. If wavelength source modulation is used then the acoustic resonance frequency will typically be twice the source modulation frequency. This is called 2f modulation and is described below. 2f modulation is utilized in a preferred embodiment of this invention but is not required for this invention.

A 2f modulation scheme, is described, for example, in Reid and Labrie, Second-Harmonic Detection with Tunable Diode Lasers—Comparison of Experiment and Theory, Applied Physics, #26, pp. 203-210, 1981, A 2f modulation has the advantage of rejecting many different sources of background noise. This modulation scheme is suitably realized by wavelength modulation of the optical source. As the optical source is swept back and forth across an absorption wavelength feature of the target analyte (with one complete cycle of the optical source wavelength going first shorter and then longer and then back over the absorption feature wavelength) which thus causes the absorption feature to be encountered twice. The detector (microphone) thus responds twice for every modulation cycle of the light source. This means that the microphone response is at twice the modulation frequency, whereas any spurious signals created at the modulation frequency will be at the source frequency and thus easily rejected by the detection instrument, which only responds to the 2f frequency.

The particular acoustic resonance frequency of the photoacoustic cell is not a critical parameter in this invention. This parameter may be chosen to satisfy a variety of system design constraints such as system size, external noise rejection, available microphones or even arbitrarily chosen. One skilled in the art of engineering can either pick an acoustic resonance frequency based on system design constraints detailed in the following paragraphs, or choose an arbitrary acoustic resonance frequency and design a PAS cell according to the constraints of this invention.

Equation (1) describes the sensitivity of a prior art cylindrical resonant photoacoustic cell, as shown in FIG. 1a, operating on the first longitudinal node, and suggests the issues facing the design engineer:

$$S_{PAS} \propto \frac{P\alpha l Q_{ac}}{V\omega} \qquad \text{Equation (1)}$$

In Equation (1) $S_{PAS}$ is the sensitivity of the PAS system, P is the optical power in the acoustic cavity, $\alpha$ is the absorption coefficient of the target analyte gas, l is the absorption path length, $Q_{ac}$ is the quality factor of the acoustic cavity, V is the volume of the acoustic cavity, and $\omega$ is the acoustic resonant frequency of the cell (as defined in paragraph 17). Equation (1) indicates that sensitivity is proportional to l (the path length) divided by V (the cavity volume). For a cylindrical resonant cavity, V divided by l is the cross sectional area of the cavity. Equation (1) suggests that theoretically a cylindrical cavity with a vanishingly small diameter would have infinite sensitivity. For the purposes of this invention, cavity will refer to the main acoustic resonator and cell will refer to the cavity with the microphone, and possible connecting tubes, attached. In practice, the applicability of Equation (1) to very small diameter resonant acoustic cells is limited by turbulence and boundary layer effects near the cell walls for very small diameter resonator tubes. I have found that a suitable diameter for the resonant cavity of a PAS system in accordance with my invention will range from about 0.1 mm to about 20 mm, preferably from about 1 mm to 10 mm, most preferably 2 to 4 mm.

Methods and systems for increasing the sensitivity of photoacoustic spectroscopy cells, while simultaneously reducing their size and the cost, are essential if widespread industrial use is to be realized. Photoacoustic systems for industrial use will preferably utilize small and inexpensive light sources, such as the semiconductor diode lasers heretofore developed for telecommunications use. Such lasers are small, relatively inexpensive, and convert electrical energy into optical energy with high efficiency. Traditional PAS cell designs are discussed in detail in books such as "Optoacoustic Spectroscopy and Detection" by Pao, Academic Press, 1977. Traditional photoacoustic sensor cells use microphones as a sensing device for the pressure waves in the acoustic cavity. As already indicated, all these prior art cell designs are predicated on the assumption that the microphone is a passive detection element and the microphone should optimally have minimal influence the cell sensitivity or cell resonance frequency. I have found, contrary to the teaching of the prior art such as "Optoacoustic Spectroscopy and Detection" by Pao, Academic Press, 1977, P. D. Goldan and Kito Goto; An acoustically resonant system for the detection of low-level infra-red absorption in atmospheric pollutants; J. Appl. Physics; Vol. 45; No. 10; pp. 4350-4355, October, 1974. F. G. C. Bijnen, J. Ruess, and F. J. M. Harren; Geometrical optimization of a longitudinal resonant photoacoustic cell for sensitive and fast trace gas detection; Rev. Sci. Instruments; Vol. 67, pp. 2914-2923; 1996, J.-P. Besson, S. Schilt, L. Thevenaz; Multigas Sensing Based on Photoacoustic Spectroscopy using Tunable Laser Diodes; Spectrochemica; Vol. 60; pp. 3449-3456; 2004. Lars-Goran Rosengren; Optimal Optoacoustic Detector Design; Applied Optics; Vol. 14; No. 8; pp. 1960-1976; August, 1975. M. Szakall, Z. Bozoki, M. Kraemer, N. Spelten, O. Moehler, and U. Schurath; Evaluation of a Photoacoustic Detector for Water Vapor Measurements under Simulated Tropospheric Conditions; Environ. Sci. Tech.; Vol. 35; No. 24; pp. 4881-4885; 2001. A. Miklos, P. Hess, Z. Bozoki; Application of Acoustic Resonators in Photoacoustic Trace Gas Analysis and Metrology; Rev. Sci. Instru., Vol. 72; No. 4; pp. 1937-1955; April 2001. M. Sigrist; Laser Generation of Acoustic Signals in Liquids and Gases; J. Appl. Phys.; Vol. 60; No. 7; pp. R83-R121; October 1986. M. Sigrist; Trace Gas Monitoring by Photoacoustic and Related Techniques; Rev. Sci. Instr.; Vol. 74; No. 1; pp. 486-490; January 2003. M. Nagale and M. Sigrist, Mobile Laser Spectrometer with Novel Resonant Multipass Photoacoustic Cell for Trace-Gas Sensing; Appl. Phys. B; Vol. 70; pp. 895-901; June 2005. S. L. Firebaugh; Miniaturization and Integration of Photoacoustic Detection; Ph.D. Thesis; MIT, May 2001, that by using the microphone impedance as part of the total acoustic network (i.e., cell including microphone) one can substantially reduce the cell size while maintaining or even increasing the detection sensitivity. In general, it is very helpful to utilize the analogies between electrical and acoustical systems, as the existing tools for solving electrical circuit problems are quite mature. This analogy will be described in great detail later, but it will be helpful to know that a volume displacement or acoustical compliance is analogous to a capacitance, while an acoustically short tube can act as an acoustic resistance and inertance which are represented electrically by resistance and inductance respectively. With these definitions in mind, reference to acoustic quantities in electrical engineering terminology should have specific meaning.

I have found that the microphone impedance may be incorporated into (combined with) the PAS cell impedance in a number of ways. One approach is to operate the PAS cell at a low frequency using tubes of a diameter much less than their length which open into buffer regions of much larger diameter or even open air, as shown in FIGS. 2 and 4. This results in the PAS cell acting like an equivalent acoustic inductance. For a resonance to also occur there must also be an equivalent acoustic capacitance to complete the energy exchange of a resonator. I have discovered that a resonant cell can be achieved by placing the microphone in the PAS cell and using the back-volume of the microphone to act as an acoustic capacitance.

PAS cells in accordance with the present invention use resonant acoustic cavities. Resonant cavities can be realized in different forms, either lumped (commonly referred to as Helmholtz resonators), or distributed. My invention is applicable to both types of cells. The distinction between lumped and distributed cavities can be described as follows. As the acoustic cavity resonant frequency increases the acoustic wavelength of the chamber decreases and the dimensions of the structure will approach a substantial fraction (e.g. an eighth or more) of an acoustic wavelength, causing the pressure and volume velocity to show significant changes along the axis of the chamber. This pressure and volume velocity variation with distance along the axis of the chamber means that the inductive and capacitive attributes can no longer be considered as lumped in particular regions of the chamber but must now be considered as distributed along the chamber (See e.g., "Theoretical Acoustics", Morse and Ingard, Princeton University Press, 1968). PAS cell geometries in accordance with the present invention can have many shapes. A preferred embodiment of a distributed system in accordance with my invention is a tube between two optical windows with auxiliary tubes branching off near the optical windows. The branch tubes in this preferred embodiment end in buffer chambers of larger diameter connected to the analyte containing fluid inlet and outlet as shown in FIG. 6. The resonant acoustic chamber be either a closed cell or an open cell. Preferably the resonant acoustic chamber is substantially cylindrical and comprises an optical window and/or an optical reflector at least one end. Provided however, the resonant acoustic chamber can in the alternative be non-cylindrical Helmholtz ("lumped") resonators are sometimes preferred for the practice of the present invention in that they permit a reduction in the size of the resonator chamber because, unlike distributed resonators, they do not require chamber dimensions which approach that of the acoustic wavelength. Reducing the size of a PAS instrument is desirable for a variety of reasons including reduced cost and weight. The dimensions of the various elements of a lumped acoustic system can be small in comparison with the wavelength of the generated sound and, when this is true, the motion of the fluid medium (usually a gas) in the system is analogous to that of a mechanical system having lumped mechanical elements of mass, stiffness and resistance. A Helmholtz resonator can be realized in a variety of configurations, two of which are shown in FIGS. 1a) and 1b). FIG. 1a) shows a Helmholtz resonator with one end open to the gas (or other fluid) containing the target analyte. The fluid in the large cavity acts as a spring, and the gas in the narrow tube acts as a mass because of the relative cross-sectional areas. The Helmholtz resonator shown in FIG. 1a), consists of a rigid enclosure of volume $V_c$, communicating with the external medium through a small opening of area S and length $l_m$. The gas in the opening is considered to move as a unit and provides the mass element of the system, the pressure of the gas within the acoustic cell changes as it is alternately compressed and expanded by the influx and efflux of gas through the opening and thus provides the stiffness element. At the opening, moreover, there is radiation of sound into the surrounding medium which leads to the dissipation of acoustic energy and thus provides one source of frictional loss.

As mentioned before, acoustic systems can be analogized to electrical systems and quantitatively solved. In an analogous electrical system the motion of the fluid medium is equivalent to the behavior of current in an electric circuit having elements of inductance, capacitance, and resistance. The electrical analogue of the pressure difference across an acoustic element is the voltage across a component of an electric circuit. The acoustic analogue of current at a point in the circuit is equivalent to the volume velocity of the fluid in the acoustic element. The latter quantity is defined in terms of the rate of volume displacement of fluid in the acoustic element.

The analogy between acoustic and electrical systems may be advantageously carried further by again considering FIG. 1a) and defining the acoustic inertance M of a cylindrical acoustic element as:

$$M = \frac{m}{S^2} \qquad \text{Equation (2)}$$

where m is the mass of the element and S is the cross sectional area of the mass in the plane through which the mass moves. Typically an acoustic mass is related to a constriction, orifice, or column of air with an area, S, and length, $l_m$. An application of this definition to a Helmholtz resonator in which the mass is a cylindrical volume of gas, $V_m$, gives:

$$M = \frac{\rho V_m}{S^2} = \frac{\rho l_m S}{S^2} = \frac{\rho l_m}{S} \qquad \text{Equation (3)}$$

where ρ is the density of the gas. Acoustic inertance is analogous to electrical inductance and has the dimensions of kg/m⁴ in the MKS system of units.

The acoustic compliance C of an acoustic element is defined as the volume displacement that is produced by the application of unit pressure. It is the analogue of electrical capacitance, (the charge appearing on a capacitor per unit of applied voltage). For an acoustic element having an enclosed volume $V_c$, such as in the Helmholtz resonator of FIG. 1a), this definition leads to:

$$C = \frac{V_c}{\rho c^2} \qquad \text{Equation (4)}$$

where lower case c is the speed of sound in the fluid, ρ is the density of the fluid (normally a gas), and $V_c$ is the volume of the acoustic cavity. The units of acoustic compliance are m⁴sec²/kg.

An element or characteristic of an acoustic system that leads to the dissipation of energy is analogous to electrical resistance. For example, a major portion of the acoustic resistance R of a Helmholtz resonator can result from the radiation of sound energy and is given by R=ρ c k²/2π, where k is 2π divided by the acoustic wavelength, It is also possible to derive expressions for the additional acoustic resistance associated with viscous forces in the fluid medium.

Helmholtz resonators are schematically represented in FIGS. 1a) and 1b). However, it should be understood that these acoustic systems may also be represented schematically by the circuit of the analogous electrical systems, i.e., FIGS. 3a) and 3b) which correspond to 1a) and 1b), respectively. In general, when it is possible to replace an acoustic system by the schematic circuit of an analogous electrical system, known solutions of the latter may be used to analyze the former. The analogies just described are those most commonly used in acoustics. However, another system of analogies known as the mobility system can sometimes also be advantageously used. In the mobility system acoustic mobility, defined as the ratio of volume velocity across, to pressure through, the acoustic system is analogous to electrical impedance, volume velocity to voltage, pressure to current, inertance to capacitance, compliance to inductance and the reciprocal of the acoustic resistance to electrical resistance.

A known embodiment for a closed PAS cell is a 'dumbbell' Helmholtz resonator as shown in FIG. 1b). In FIG. 1b) the relatively large gas volumes on each end of the dumbbell act as springs and the central narrow tube acts as a mass which resonates with the springs. Typically in prior art designs a light source excites the gas in one of the tube ends and a microphone is located in the opposite end. Because PAS cell sensitivity for most configurations is inversely proportional to volume, the large gas volumes in the two ends of the dumbbell tend to limit cell sensitivity.

My invention is substantially independent of the optical source power. Light sources for my invention are preferably, but not limited to, coherent, wavelength (frequency) modulatable continuous wave lasers. Alternative sources may be incoherent, or pulsed lasers which can be either directly or indirectly modulated. Likewise, although not preferred, the light source may be energy modulated. Collimated LED sources are also suitable for the practice of my invention. Sources of a wide power range are suitable. Preferably the power will range from about microwatts up to hundreds of milliwatts.

Both lumped and distributed acoustic cells fall within the scope of my invention provided only that the cavity impedance at the interface to the microphone has an absolute impedance magnitude within a factor of three (i.e., ⅓ to 3 times that) of the microphone impedance magnitude and of opposite reactance to the microphone reactance. A preferred embodiment is an acoustic cylinder of diameter between about 1 and 4 mm with a length of approximately 40 to 100 mm between the optical windows. My invention also applies to PAS operation with liquid or solid substrates. Examples of PAS operation using prior art cell designs for detecting materials other than gases can be found in J. Pelzl, K. Klein, and O. Nordhaus, "Extended Helmholtz Resonator in Low-Temperature Photoacoustic Spectroscopy", *Applied Optics, Vol.* 21, No. 1, January 1982, pp. 94-99.

My invention is directed to a photoacoustic cell wherein the acoustic impedances of both the acoustic sensor (i.e., the microphone) and the PAS chamber significantly interact. Since impedance equals pressure divided by volume velocity, by designing the cell and choosing the sensor so that the acoustic impedances of the chamber and the sensor are of substantially the same order of magnitude they will significantly interact. This permits a significant reduction in the acoustic chamber size and thereby significantly increases the sensitivity of the PAS cell. As indicated, I have found that the impedance of the microphone should range from about one-third (⅓) to about three (3) times the impedance of the resonant chamber at the point where the microphone attaches to the chamber and at the acoustic frequency used for detection. I have further discovered that the use of the microphone as part of the resonant structure, e.g., as shown in FIG. 6, is a highly effective way of minimizing chamber volume.

I have found that if the tube (acoustic chamber) dimensions are chosen correctly (as defined herein) a mode will occur which is significantly lower in frequency than the first half-wavelength mode. For the purposes of this invention the tube dimensions are chosen so that its acoustic impedance is substantially equal in magnitude to (i.e., ⅓ to 3×) the microphone acoustic impedance at the desired resonance frequency. If the microphone impedance is capacitive at the desired resonance frequency then the chamber acoustic impedance must be inductive in order for it to resonate with the microphone impedance. This lowest order mode uses the back volume of the microphone as a spring and the gas in the tube as a mass. The tube length should be maximized for the greatest optical power absorption. Suitable lengths will range from about 20 mm to 200 mm, especially 40 mm to 100 mm. However, the tube diameter and length are ultimately determined by the requirement to have the cavity reactance substantially match the microphone reactance. The resulting resonant mode can correctly be called a Helmholtz resonance because it depends on the lumped properties of the gas mass in the tube and the spring constant of the microphone back volume. Because this realization permits a significant reduction in the PAS chamber volume it therefore tends to maximize sensitivity as shown by Equation 1. Although larger chamber volumes are suitable for the practice of my invention, I have found that excellent sensitivity can be achieved with small cavity volumes in the range of from about 0.1 cc to 1.0 cc. For example, by using the compliance from the back-volume in a microphone as the equivalent spring in a resonant cavity the $V_c$ section in FIG. 1a can be replaced with a microphone, thus permitting greatly reducing the size of the acoustic resonator chamber. This is because the diaphragm of a microphone combines with the volume of air behind the microphone (i.e., the "back-volume") to create an equivalent acoustic capacitance equal to a much larger volume chamber containing air alone.

BRIEF DESCRIPTION OF THE DRAWINGS

In FIG. 1 S, $V_m$ and $l_m$ denote the cross sectional area, volume and length of the inlet port, respectively

FIG. 3a) represents the cavity in FIG. 1 a) and has the fluid mass in the cylindrical port as $L_{port}$, the total loss in the resonator as $R_{res}$, and the cavity compliance as $C_c$. Note that the port being open to the air acts as a ground connection in the electrical analogy. FIG. 3b) represents the electrical analog of the device in FIG. 1 b) with $L_{port}$, $C_{c1}$, $C_{c2}$, and $R_{res}$ having the same meanings as in FIG. 3a. and $C_{c1}$, and $C_{c2}$, both denoting compliance (or equivalent acoustic capacitance).

DETAILED DESCRIPTION OF THE INVENTION

Figure 1:
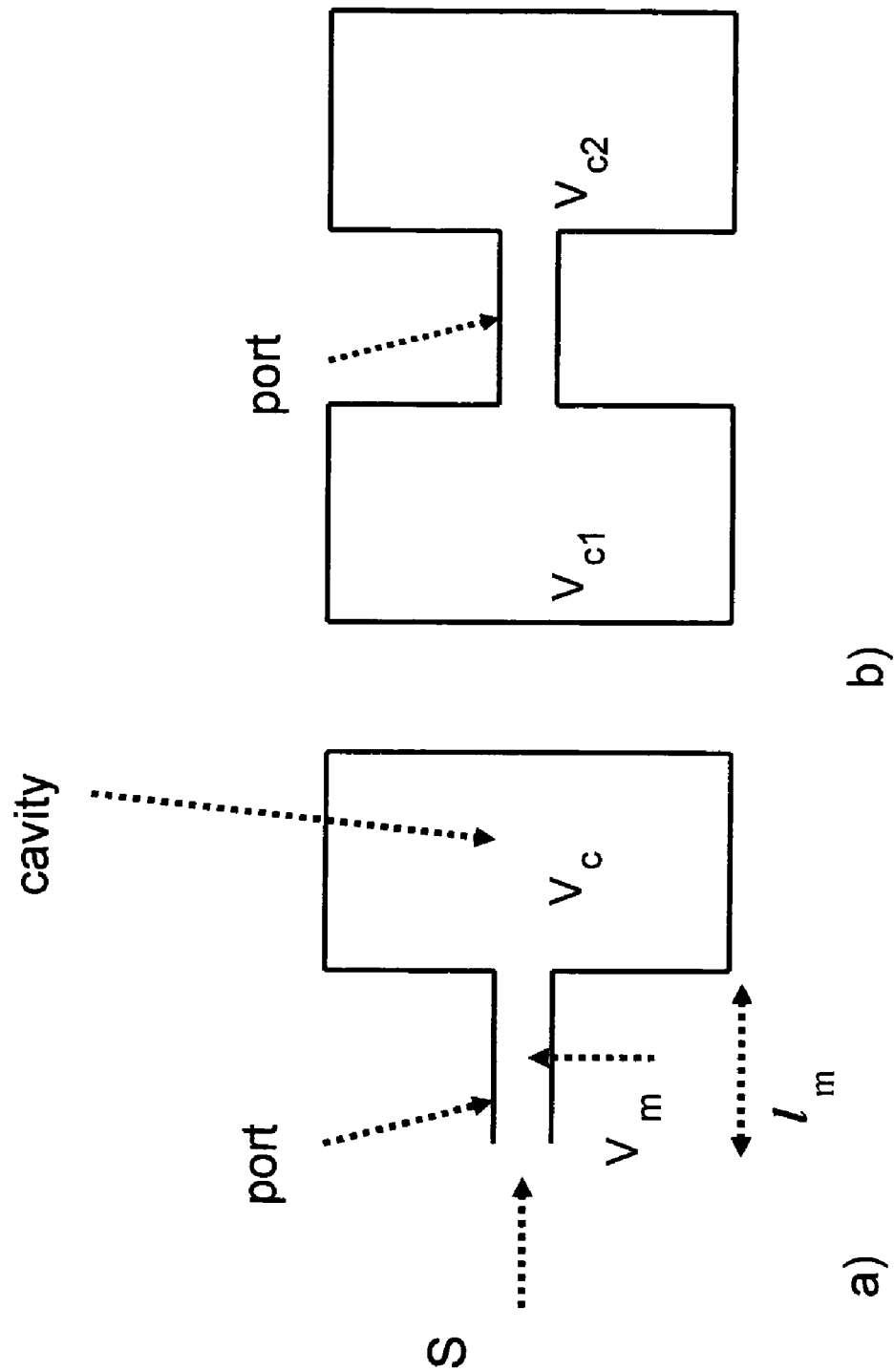
FIG. 1. Helmholtz resonators. Resonator a) is a prior art style with one end of the chamber open to the air. Resonator b) is another prior art style which is more suited to the closed environment of most PAS cells.
Figure 2:
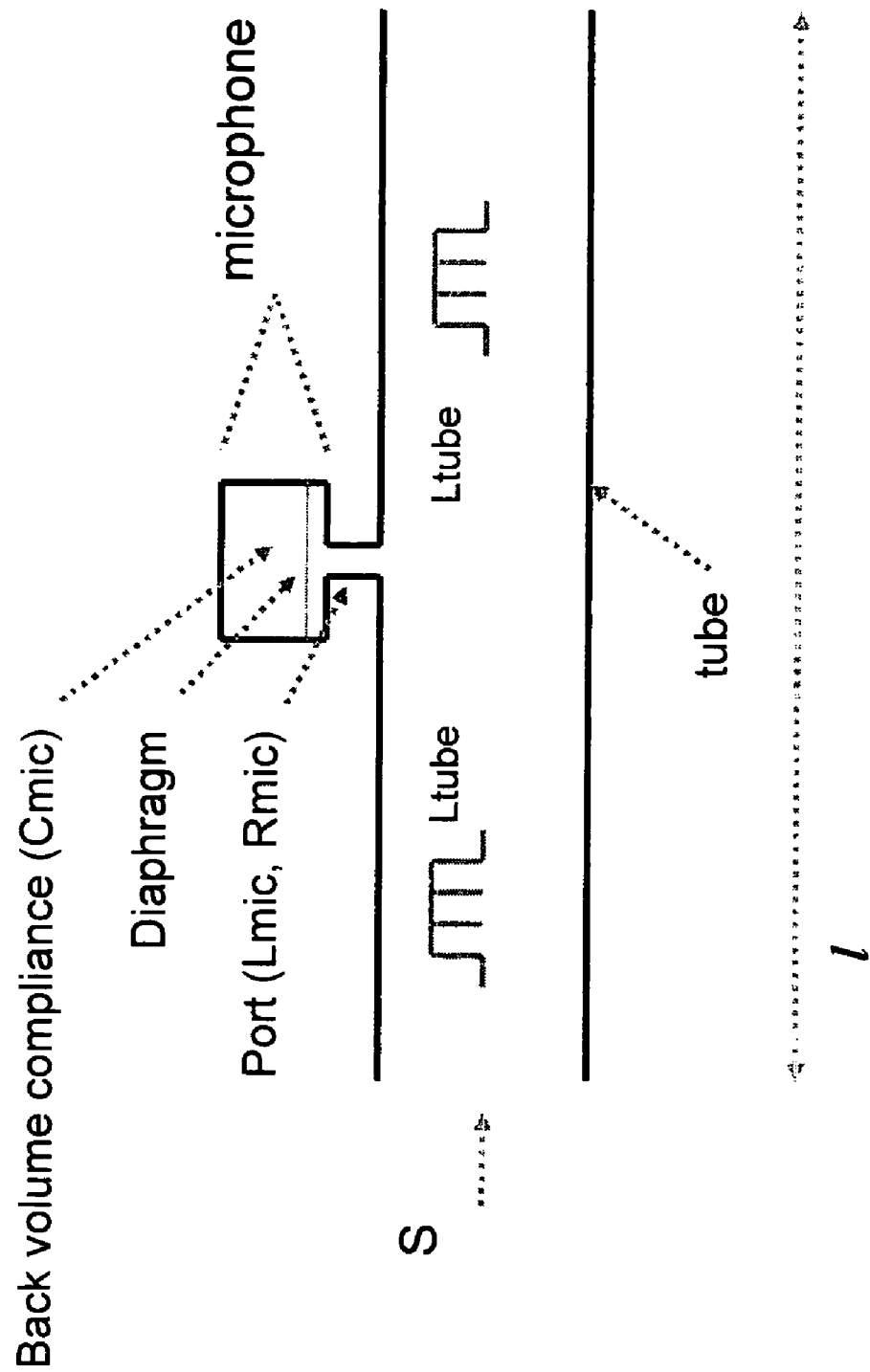
FIG. 2 shows an acoustic resonator with a chamber having open ends and a microphone. At very low frequencies each tube section acts as an acoustic inductance, $L_{tube}$. S again denotes the cross sectional area of the tube.
Figure 3:
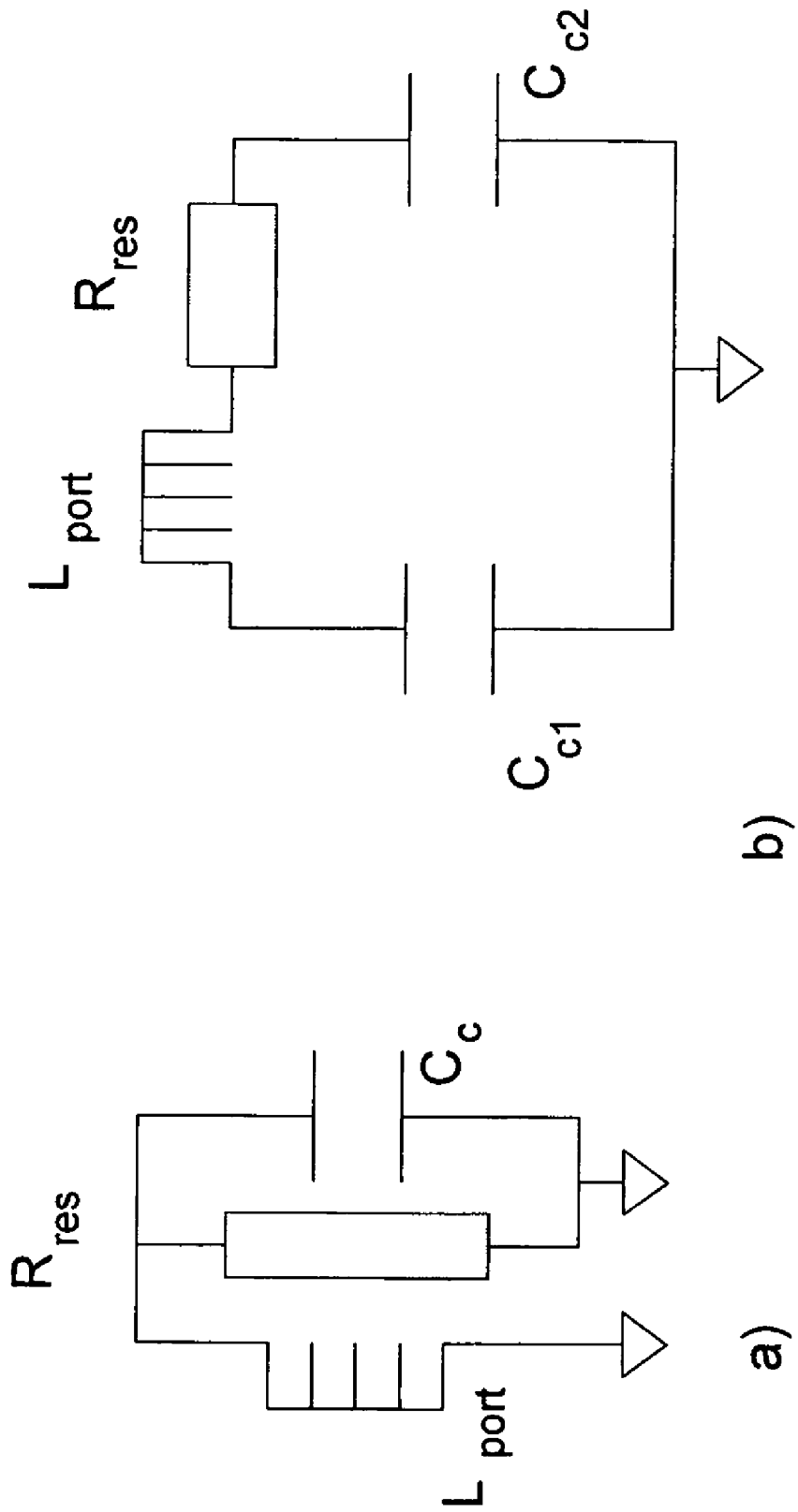
FIG. 3 shows the electrical models analogous to Helmholtz resonators 1a) and 1b).
Figure 4:
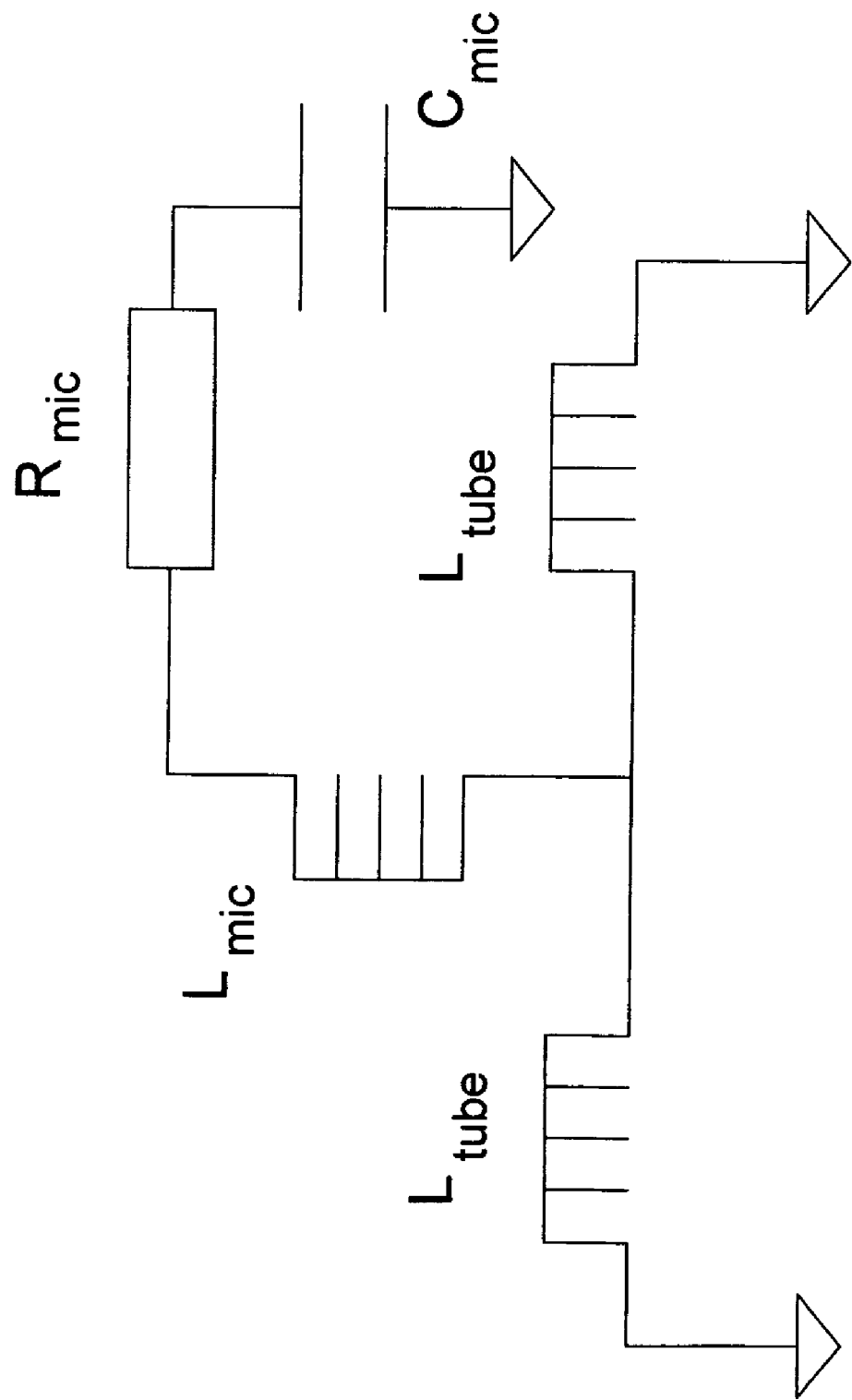
FIG. 4 shows the electrical analog model of the lowest mode of the resonator shown in FIG. 2. At low frequencies the tube appears only as a fluid mass with the open ends of the tube appearing as acoustical grounds. Microphone losses dominate in this model with L, R and C denoting acoustic equivalent inductance, resistance and capacitance, respectively

The present invention recognizes that the interaction between the microphone acoustic impedance and the cell acoustic impedance can be used to great benefit if a photoacoustic chamber is properly designed, as previously described and also in further detail below. In a first embodiment, a cell such as that shown in FIG. 2 has a microphone inside a tube. The lowest order resonance for this configuration has an analogous electrical circuit as shown in FIG. 4. The elements corresponding to the microphone are labeled with the subscript "mic". The microphone can be represented by a series LRC circuit and at low frequencies the tube can be represented as an air mass just as the port is represented in FIG. 1a. At resonance the various elements of the network in FIG. 4 can be reduced to an equivalent circuit as shown in FIG. 3a). The circuit of FIG. 3a) is applicable to any parallel resonant network, including Helmholtz resonators. The preferred design of a PAS cell in accordance with this invention requires the cell acoustic reactance to be substantially equal and opposite to that of the microphone at the desired resonance frequency. Furthermore, the cell diameter and length can be adjusted to maximize the absorption of the optical signal while keeping within such length and volume constraints as are required by other system constraints e.g., aperturing and heating of the resonant chamber walls by the light beam. Finally, the vent lengths and diameters can also be optimized, by iterative design, computer algorithms, or any other method known to those skilled in the art, so that the microphone output is maximized for a given optical input power.

Figure 8:
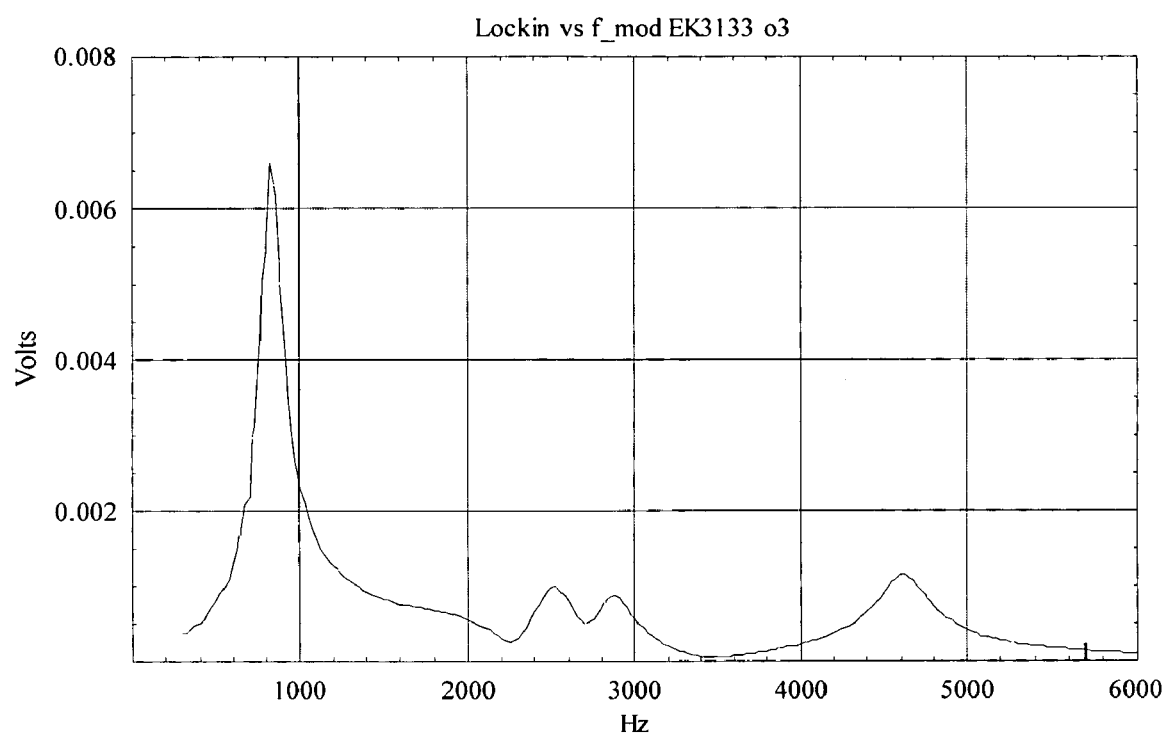
FIG. 8 illustrates results obtained with an embodiment of the present invention having a 2 cm long resonator chamber showing a first longitudinal mode at 4.6 kHz source modulation frequency, which is half of the actual acoustic frequency, lower frequency modes at around 2.6 kHz source modulation frequency are due to resonator and buffer lengths, and a lowest frequency (integral-mic) mode at 800 Hz. The actual acoustic resonances occur at twice the source modulation frequency due to the use of 2f detection. Note how much greater the response is from the integral-mic mode (approximately 5 times the longitudinal mode). This integral microphone mode shown here is an example of the present invention.

Because the back volume of the microphone provides the dominant compliance for this resonator element the system resonance occurs at a significantly lower frequency than the first longitudinal mode of the tube. This is because the microphone diaphragm and back volume can exhibit a compliance greater than that distributed through the tube (acoustic chamber) volume. One of the reasons for the high sensitivity of my invention is that lowering the resonant frequency of the cell increases the sensitivity of the cell (as seen from Equation 1). Results shown in FIG. 8 indicate a PAS cell frequency response with the microphone-integral mode (resonance at 800 Hz) and the first order longitudinal mode (resonance at 4600 Hz). The frequencies shown in FIG. 8 are the modulation frequencies of the light source for the measurement system. Because the measurement system uses a 2f modulation scheme the actual acoustical resonances are at twice the frequencies shown in the FIG. 8.

Figure 5:
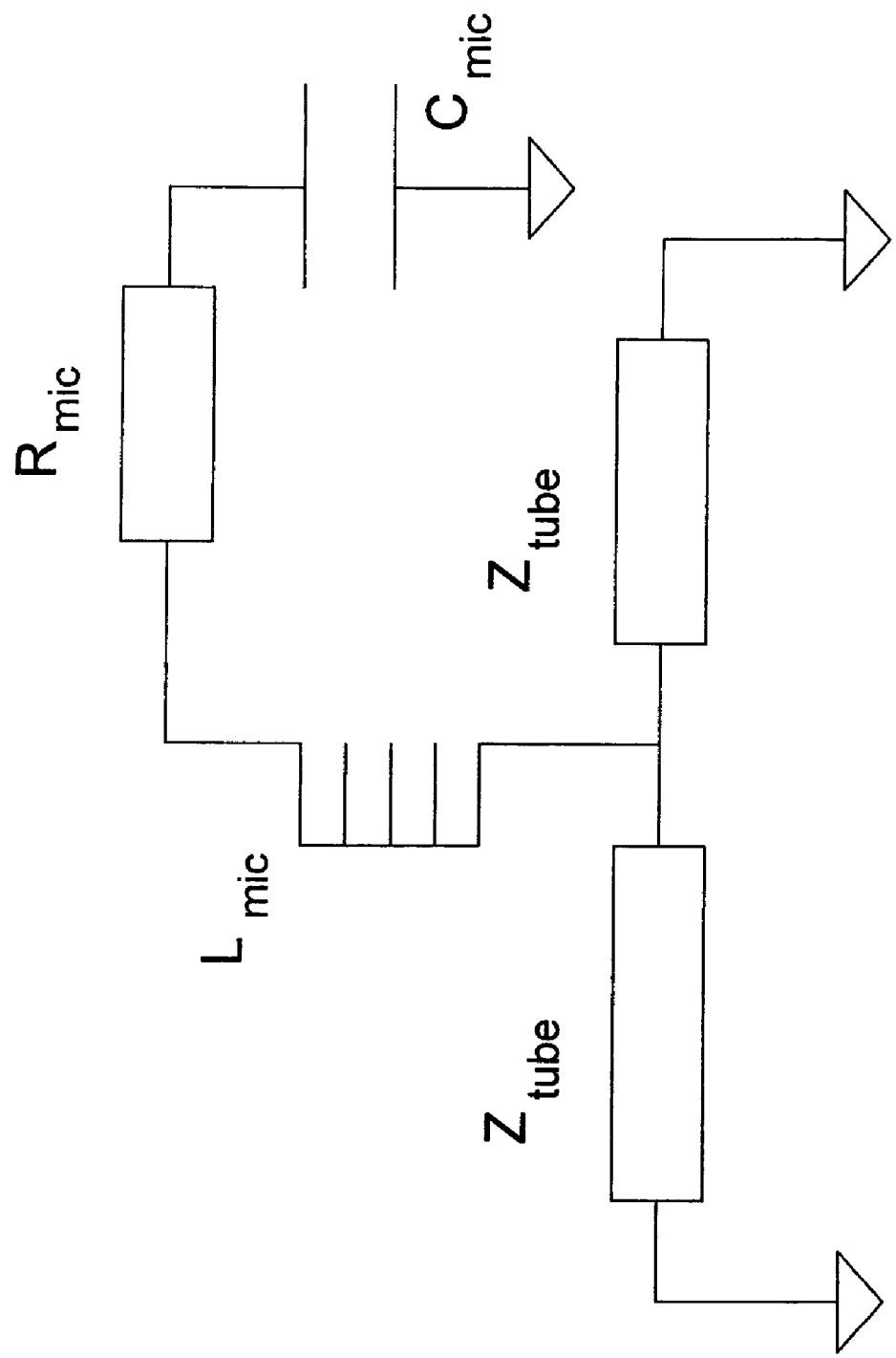
FIG. 5 illustrates an electrical analog model of any longitudinal mode of the resonator in FIG. 2. $Z_{tube}$ is the characteristic impedance of the tube.
Figure 7:
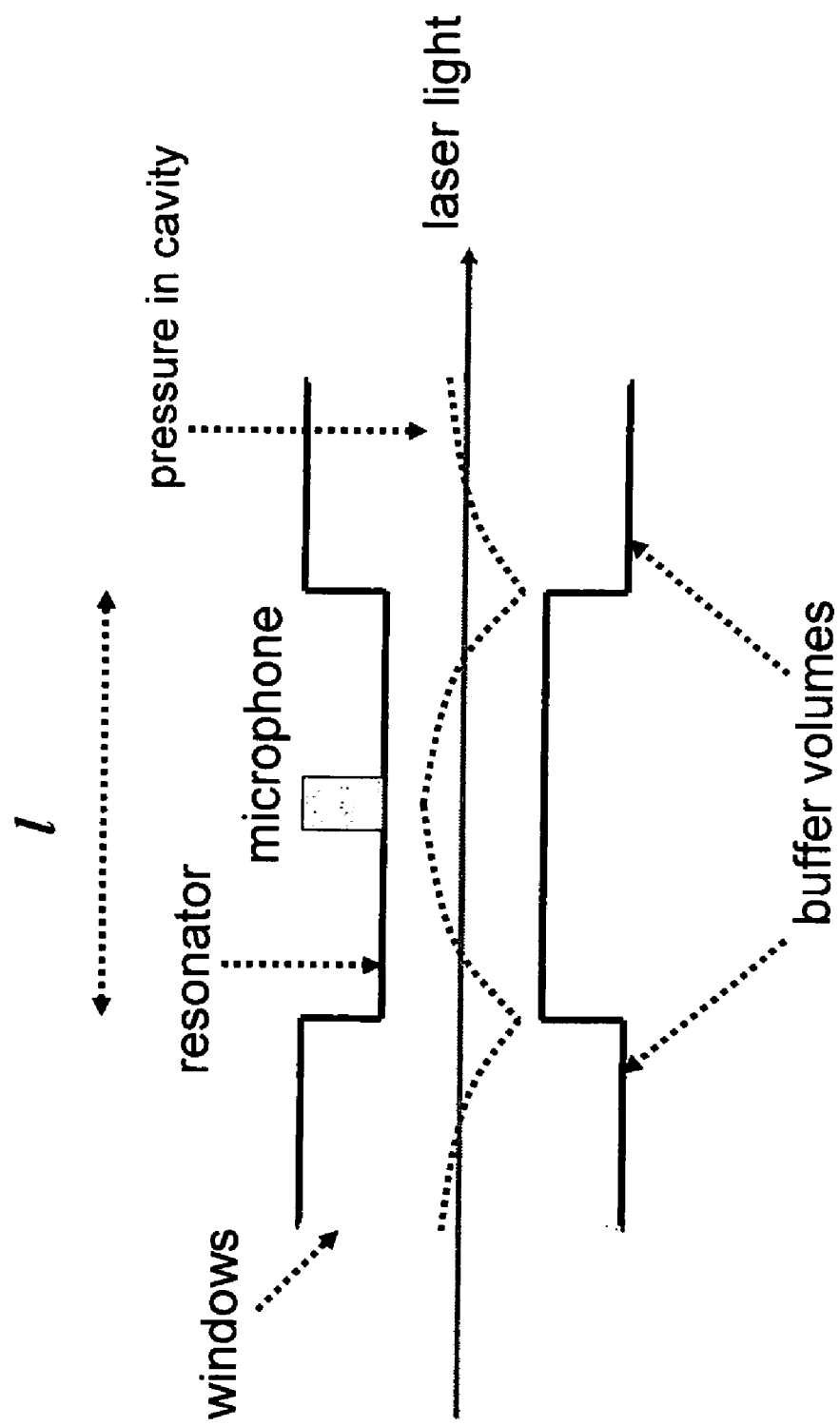
FIG. 7 shows a prior art design for a photoacoustic cell. Buffer volumes are used for defining cavity length and for acoustical filtering. The resonator has a length, l, and area, S. Typically gas lines are connected to the buffer volumes to allow gas to flow through the cell.

The results shown in FIG. 8 are for a cell that is similar to that shown in FIG. 7. FIG. 8 shows the integral-mic resonance as the lowest frequency resonance as well as other resonances at higher frequencies. The integral-microphone mode shows an approximately 5 fold increase in sensitivity over the first longitudinal mode. While FIG. 4 describes the lowest order mode for a simple cell, the FIG. 5 embodiment is useful for describing the first, and higher, longitudinal modes of a relatively small diameter cylindrical tube. The relatively small diameter (compared to the length) ensures that only longitudinal modes exist. In FIG. 5 the tube is no longer represented by an equivalent mass, but rather by a transmission line of impedance pc/S. Also, as the frequency increases the microphone equivalent circuit, as shown in FIG. 5, goes through resonance and appears resistive and inductive rather than capacitive and resistive. As the frequency increases the resistance of the microphone can thus form an appreciable part of the loss of small diameter cells, but the resonant frequency is increasingly determined by the length of the cell.

Figure 6:
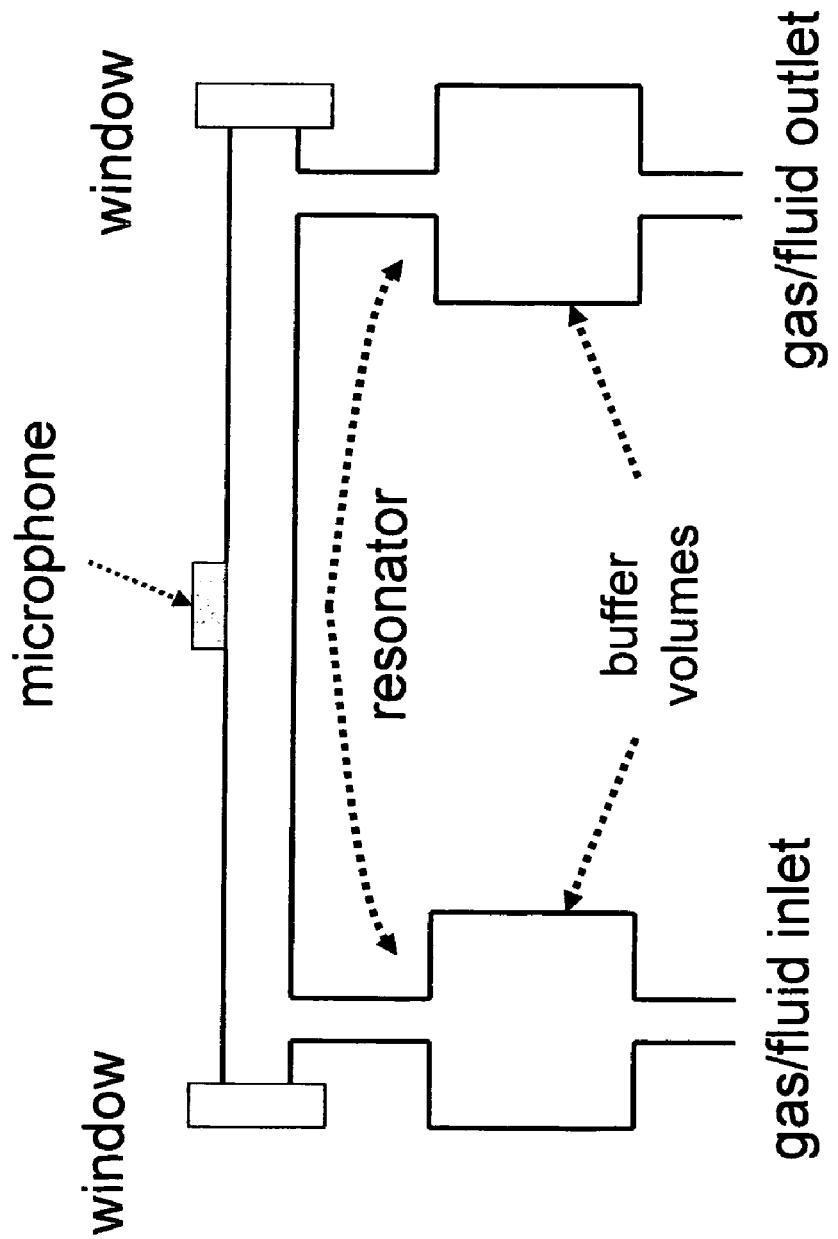
FIG. 6 shows an embodiment of the present invention used to connect the acoustic chamber (cavity) to fluid lines. Buffer volumes serve to define cavity length and for acoustical filtering.
Figure 9:
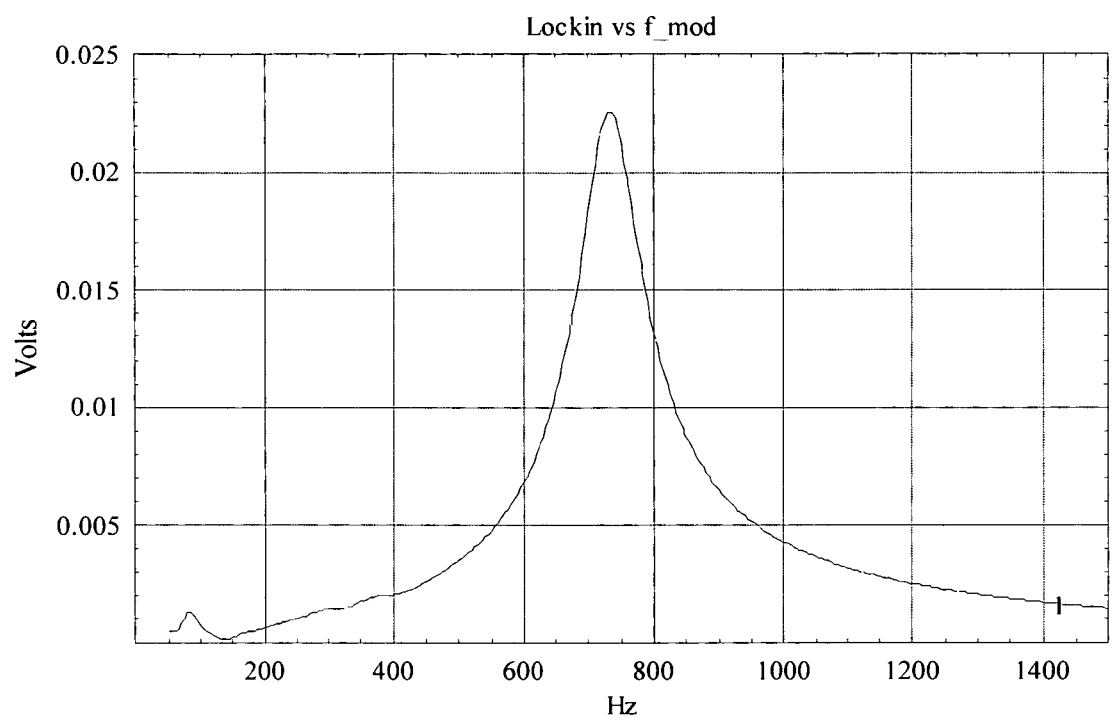
FIG. 9 shows the results obtained with a 6 cm long resonator chamber in another embodiment of the present invention. The y-axis is the microphone output and the x-axis is the source modulation frequency. The response to atmospheric moisture levels is equivalent to a cell constant of 15,000, which is superior to the results obtained with prior configurations.

In order to understand why the accuracy of the resonant frequency is determined increasingly by the length of the cell as frequency is increased, one needs to consider how the resonant frequency is affected by a distributed circuit. In a lumped system, the inductance or capacitance at any point in a circuit is independent of frequency. In distributed circuits the reflections of pressure and volume velocity waves cause the net inductance or capacitance at a given point in the structure to vary with frequency. Depending on the boundary conditions (specifically whether the ends of the acoustic resonator form an acoustic high or low impedance) longitudinal modes in distributed systems will resonate when the structure is an odd multiple of quarter wavelengths, or an even multiple of half wavelengths. As frequencies increase the impedance change in the structure also increases with frequency. This means that an impedance perturbation due to a microphone present in the structure can cause a large resonance frequency shift at low frequencies because the impedance change at any point is a gradual function of frequency. At high frequencies the impedance change at any point is rapid with frequency and the complimentary impedance to a microphone is quickly reached, thereby allowing resonance to occur. Thus, as frequency increases the resonant frequency of a structure is more and more defined by its physical length While open air measurements with a PAS cell are useful in certain situations, the preferred configuration for process gas evaluation is to have a sensor in the inlet gas line or at a T-junction on the gas line. While many adaptations of a PAS cell are possible for gas lines, the most common is to configure the PAS cell so that the gas inlets and outlets enter through and exit from the buffer volumes. For my PAS cell one preferred embodiment is shown in FIG. 6. This configuration includes a resonant chamber with connections to the gas flow lines and windows for the laser light to pass through the cell. A resonator in accordance with this configuration is suitably made of 2 mm diameter tubing with additional sections of 2 mm tubing at a right angle forming connections to the buffer volumes. The distance between the windows is e.g., 6 cm. The buffer volumes are located between the resonator and the gas flow lines and act as acoustic noise filters and serve to provide the an acoustic impedance to the resonant cell which maximizes the performance of the cell. The response of the cell shown in FIG. 6 is shown in FIG. 9. The results are for an atmospheric moisture level of 10,000 ppm and a source laser light wavelength of e.g., 1392.53 nm. The x-axis is in volts from the microphone and the y-axis is the laser light source modulation frequency. This result represents a cell constant, as defined in Equation (5), below, on the order of 15,000, which is significantly superior to results achievable with known prior art PAS cell designs. Even very large (17 cm long by 6 mm diameter), prior art cells achieve a cell constant of no more than about 13,000. The cell constant obtained by the previously-cited Hungarian workers was only 2000. The cell constant of a PAS cell is defined by $$C_c = \frac{P_a}{\alpha P} \qquad \text{Equation (5)}$$

where $P_a$ is the pressure in Pascals, $C_c$ is the cell constant in Pa cm/W, $\alpha$ is the molecule absorbance in inverse cm, and P is the optical power available in watts at the absorbing wavelength.

Optimal performance of a PAS cell in accordance with my invention is achieved when the impedance of the main tube (resonant cavity) interacts with the microphone impedance to thereby maximize the microphone signal. This is done by operating at a frequency where the microphone acoustic capacitive reactance is greater than 2 times the acoustic resistance and the net acoustic impedance to the microphone is inductive. As noted before, this interaction occurs when the acoustic chamber impedance at the interface to the microphone has an absolute impedance magnitude within a factor of three (i.e., ⅓ to 3 times that) of the microphone impedance magnitude and of opposite reactance to the microphone impedance. A further advantage is achieved because the absorbed light energy is proportional to the distance between the windows. Another advantage in the PAS cell design of the present invention is the acoustic Q of the cell. The acoustic Q is defined as the resonant frequency of the cell divided by the half-power bandwidth of the cell. The half-power bandwidth of a cell is the bandwidth, or frequency difference, between the half-power transmission points of the cell relative to the peak power transmission at resonance. The actual physics behind the cell Q is that Q is the energy stored divided by the energy dissipated per radian cycle ($\omega=2\pi f$). Q is proportional to the decay time of the PAS cell, so that a larger Q means a longer decay time and the fact that the acoustic wave within the cell bounces back and forth more times for a given amplitude reduction. A higher acoustic Q means a reduced acoustic bandwidth PAS cell which helps with noise rejection because noise outside the PAS cell bandwidth is rejected. However, a narrower bandwidth will also mean that the source modulation frequency should be more closely controlled to achieve an optimal response. Changes in temperature and gas composition within the cell will change the resonant frequency of the cell. This is because the speed of sound is affected by both temperature and gas composition, so the source modulation frequency must change if cell resonance is to be maintained under variations in temperature and gas composition, as shown in Equation (6). In Equation (6) $\gamma$ is the adiabatic gas constant (e.g., about 1.4 for air) and M is the molar mass of the gas, both of which depend on the gas composition. In Equation (6) R is the universal gas constant (8.31 in MKS units) and T is the gas temperature in degrees Kelvin and c is the speed of sound.

$$c = \sqrt{\frac{\gamma RT}{M}} \quad \text{Equation (6)}$$

By examining FIG. 4 and the associated optical path length of the absorbing gas, a sensitivity equation can be derived for this PAS cell. Equation (7) defines the cell constant for FIG. 4.

$$C_c = 100 \frac{(\gamma - 1) l_L (2 l_c / S_c + 3 l_v / S_v)}{6 c^2 C_{mic} R_{mic}} \quad \text{Equation (7)}$$

where $C_c$ is the cell constant, $l_L$ is the optical path length, $l_c$ is the cavity length, $S_c$ is the cavity cross-sectional area, $l_v$ is the vent path length, $S_v$ is the vent cross sectional area, c is the speed of sound in the gas, $C_{mic}$ is the microphone acoustic compliance, and $R_{mic}$ is the microphone's acoustic resistance. With reference to FIG. 6, $l_L$ is the distance between the two windows in a single-pass cell, $l_c$ is the distance between vent centers, and l is the length of each vent.

Another preferred embodiment of this invention uses the doubly-resonant PAS method described in U.S. Pat. No. 7,263,871.

I claim:

1. A photoacoustic spectroscopy instrument comprising:
   i) a modulatable light source which provides optical radiation at an absorption wavelength of a target analyte;
   ii) a resonant acoustic chamber for containing said analyte;
   iii) a microphone positioned within said chamber whereby the acoustic reactance of the microphone is a substantial factor in determining the acoustic resonant frequency of the acoustic chamber and wherein the magnitude of the acoustic reactance of the microphone is at least two times the acoustic resistance of the microphone.

2. The instrument of claim 1 wherein said light source is a frequency modulated laser.

3. The instrument of claim 2 wherein said laser is a continuous wave laser.

4. The instrument of claim 1 wherein said light source is a phase modulated laser.

5. The instrument of claim 4 wherein said laser is a continuous wave laser.

6. The instrument of claim 1 wherein said light source is a fixed frequency laser using direct or external amplitude modulation.

7. The instrument of claim 1 wherein the amplitude of said optical radiation is modulated.

8. The instrument of claim 1 wherein said microphone is an electret.

9. The instrument of claim 1 wherein said microphone is an acoustic transducer having an acoustic impedance within a factor of 3 of the cavity impedance at the point where the microphone attaches to the cavity and also at the resonant frequency used for detection.

10. The instrument of claim 1 wherein said resonant acoustic chamber is a Helmholtz or other lumped resonator.

11. The instrument of claim 1 wherein said resonant acoustic chamber is a distributed resonator.

12. The instrument of claim 1 wherein said resonant acoustic chamber comprises both lumped and distributed elements.

13. The instrument of claim 1 wherein said resonant acoustic chamber is a closed cell.

14. The instrument of claim 1 wherein said resonant acoustic chamber is an open cell.

15. The instrument of claim 1 wherein said resonant acoustic chamber is substantially cylindrical and comprises an optical window at least one end.

16. The instrument of claim 1 wherein said resonant acoustic chamber is substantially cylindrical and comprises an optical reflector at least one end.

17. The instrument of claim 1 wherein said resonant acoustic chamber has a diameter ranging from about 1 to 4 mm and a length ranging from about 40 to about 100 mm.

18. The instrument of claim 1 wherein said resonant acoustic chamber has a volume ranging from about 0.1 cc to 1.0 cc.

19. The instrument of claim 1 wherein said resonant acoustic chamber is non-cylindrical.

20. The instrument of claim 1 wherein the back volume of the microphone provides the dominant system compliance relative to the acoustic chamber.

21. The instrument of claim 1 wherein the light source is wavelength modulated so as to sweep back and forth across an absorbance wavelength of a target analyte present within the chamber.

* * * * *